United States Patent [19]

Lerner

[11] Patent Number: 4,574,805

[45] Date of Patent: Mar. 11, 1986

[54] INSTRUMENT FOR SKIN SURGERY AND METHOD FOR USING SAME

[75] Inventor: Seth P. Lerner, Coralville, Iowa

[73] Assignee: University of Iowa Research Foundation, Iowa City, Iowa

[21] Appl. No.: 542,278

[22] Filed: Oct. 17, 1983

[51] Int. Cl.$^4$ .............................................. A61B 17/08
[52] U.S. Cl. ................................................ 128/334 R
[58] Field of Search ......................... 128/334, 354, 18

[56] References Cited

U.S. PATENT DOCUMENTS

| | | |
|---|---|---|
| 905,007 | 11/1908 | Sether . |
| 933,024 | 10/1933 | Nagelmann .......................... 128/334 |
| 2,213,830 | 9/1940 | Anastasi . |
| 2,504,202 | 4/1950 | Kadavy . |
| 2,818,866 | 1/1958 | Thomas ............................... 128/334 |
| 2,895,478 | 7/1959 | Post ...................................... 128/334 |
| 2,998,649 | 9/1961 | Miller . |
| 3,090,386 | 5/1963 | Curtis ................................... 128/334 |
| 3,349,772 | 10/1967 | Rygg . |
| 3,842,840 | 10/1974 | Schweizer ............................ 128/334 |

*Primary Examiner*—Gene Mancene
*Assistant Examiner*—Wenceslao J. Contreras

*Attorney, Agent, or Firm*—Zarley, McKee, Thomte, Voorhees & Sease

[57] ABSTRACT

The instrument for skin surgery of the present invention comprises forceps having a pair of oppositely positioned legs. One of the legs has a hook positioned adjacent its distal end and the other of the legs has an opening therein for receiving the hook so that the two legs of the forceps may be brought together into facing engagement. The method of the present invention comprises gripping the skin adjacent the edge of an incision between the two leg members with the hook retentively engaging the subcutaneous tissue inside the wound, and with the distal end of the other leg member engaging the outer surface of the exterior skin layer. The skin is then everted adjacent the incision and a surgical needle is inserted into the subcutaneous tissue until the point of the needle has passed through a portion of the subcutaneous tissue and has exited therefrom. The surgeon then releases the grip of the skin from between the first and second leg members and uses it to grip the pointed end of the needle between the distal ends of the first and second leg members. The instrument is then used to pull the pointed end of the needle until the needle has exited from the subcutaneous tissue.

6 Claims, 8 Drawing Figures

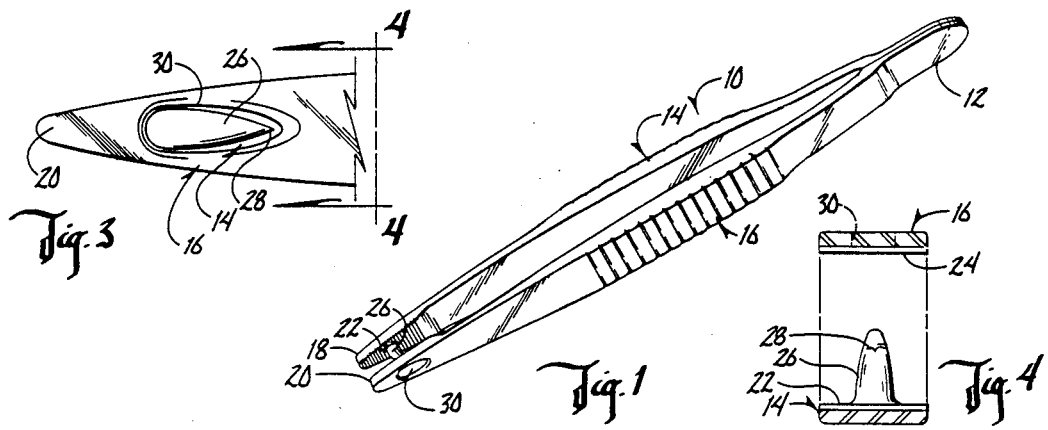
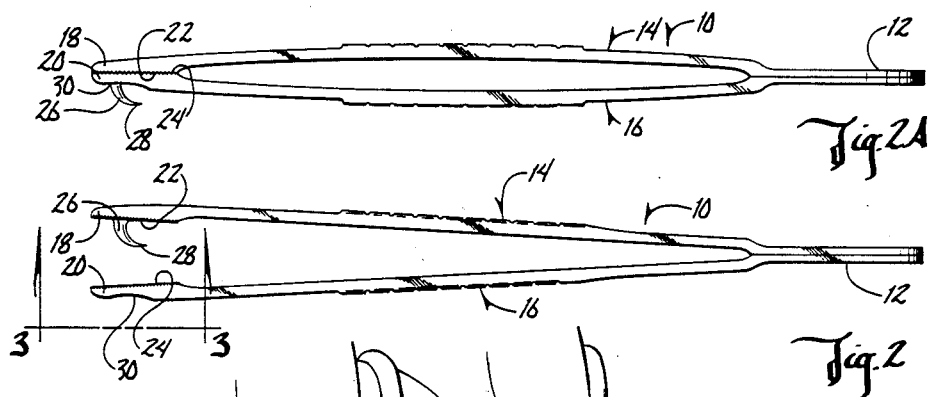
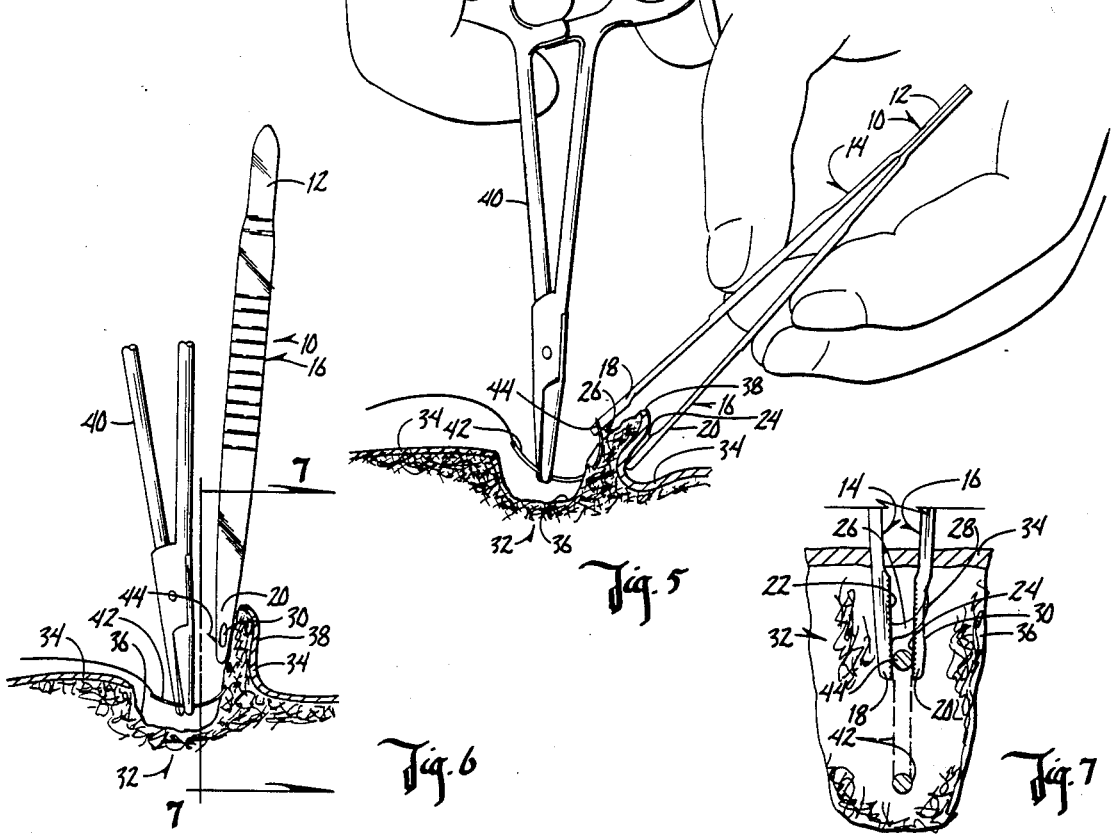

INSTRUMENT FOR SKIN SURGERY AND METHOD FOR USING SAME

BACKGROUND OF THE INVENTION

This invention relates to an instrument for skin surgery and a method for using the same.

When doing skin surgery, the surgeons presently use an instrument called a skin hook to properly align the skin edges during stitching. This minimizes damaging the skin in such a manner as to increase the amount of scar formation.

Presently used skin hooks include a long handle with a hook at one end. The hook is inserted into the subcutaneous tissue within the wound, and is used to evert (turn inside out) the skin edge so that the subcutaneous tissue is exposed for stitching. The stitch is commenced by grasping a needle in a needle holder and by inserting the needle into the subcutaneous tissue which has been exposed by the skin hook. Next, the operating physician removes the skin hook while holding the needle in place with the needle holder. A second instrument must be obtained from the tray, and is used to grasp the needle point. The needle point is then pulled through with the second instrument. In order to commence the next stitch, the operating physician must again switch back to the skin hook for everting the skin for the next stitch.

When one uses the above method, difficulty is often encountered in picking up the needle and pulling it through to complete the suture. This is particularly true when dealing with deeper sutures and may require the services of an assistant. The above maneuvers overcome this problem, but they are difficult, time consuming and energy wasting. Preferably, three hands are required to accomplish the above procedure.

Therefore, a primary object of the present invention is the provision of an improved instrument for skin surgery and method for using same.

A further object of the present invention is the provision of a device which will eliminate the necessity for three hands in the surgery procedure for forming subcutaneous stitches.

A further object of the present invention is the provision of an improved surgery instrument which permits easier and more precise control of the outer skin edge during the stitching.

A further object of the present invention is the provision of an instrument which is economical to manufacture, simple in construction and efficient in operation.

SUMMARY OF THE INVENTION

The present invention utilizes a pair of forceps having two spaced apart legs. Adjacent one end of one of the legs is an inwardly presented hook which faces the opposite leg. The opposite leg has a hole therein for receiving the hook. The hook is spaced upwardly approximately 3-5 millimeters from the end of the forceps. The method for using the instrument comprises first placing the skin hook in the subcutaneous tissue within the wound, and placing the opposite leg of the forceps on the outside of the skin layer. The instrument is then used to evert, or turn inside out, the skin adjacent the edge of the wound. This exposes the subcutaneous tissue for the stitch. A needle holder with a needle therein is used to force the needle into the subcutaneous tissue to a point where the pointed end of the needle is exposed but not yet removed from the skin. Then, the instrument is released from its grip of the edge of the skin and the instrument is used to grasp the free end of the needle. Because the hook in the instrument fits within a hole on the opposite leg, the two legs are permitted to come together so that they can grip the free end of the needle. Once the free end of the needle is gripped, it is pulled on through to complete the stitch.

The above procedure can be accomplished with two hands since the surgical instrument of the present invention can be used both for everting the skin and for grasping the free end of the needle.

BRIEF DESCRIPTION OF THE FIGURES OF THE DRAWINGS

FIG. 1 is a perspective view of the surgical instrument of the present invention.

FIG. 2 is a top plan view of the instrument.

FIG. 2A is a top plan view of the instrument showing the legs of the instrument in a closed position.

FIG. 3 is a sectional view taken along line 3—3 of FIG. 2.

FIG. 4 is a sectional view taken along line 4—4 of FIG. 3.

FIG. 5 is a sectional view showing the use of the instrument in everting the skin layer adjacent an incision.

FIG. 6 is a view similar to FIG. 5, showing the instrument grasping the free end of the needle.

FIG. 7 is a sectional view taken along line 7—7 of FIG. 6.

DETAILED DESCRIPTION OF THE PREFERRED EMBODIMENT

Referring to the drawings, the numeral 10 generally designates the surgical instrument of the present invention. Instrument 10 comprises a central handle portion 12, having a pair of diverging legs 14, 16, extending therefrom. Legs 14, 16 each are provided with a distal end 18, 20, respectively. A flat serrated surface 22 is provided on the interior surface of distal end 18 and a similar flat serrated surface 24 is provided on the interior surface of distal end 20.

Attached to leg 14 at a point spaced upwardly from distal end 18 is a skin hook 26 which extends toward leg 16 and which includes a pointed end 28 pointed in the direction of handle portion 12. The preferred distance for hook 26 to be spaced from distal end 18 is approximately three to five millimeters.

Leg 16 includes a tear drop shaped opening 30 which is sized to receive hook 26 when legs 14, 16 are forced together in the position shown in FIG. 2A. Opening 30 is in registered alignment with skin hook 26.

FIG. 2 shows the instrument in its normal position. In this position, hook 26 is spaced from leg 16. Legs 14, 16 are resilient so as to be yieldably movable from the open position shown in FIG. 2 to the closed position shown in FIG. 2A. In the closed position, the serrated flat portions 22, 24 are in facing engagement with one another, and hook 26 is received within opening 30.

FIGS. 5, 6 and 7 illustrate the use of the instrument in making surgical stitches. An incision or wound 32 is shown in a skin layer 34 having subcutaneous tissue 36 therebelow.

The instrument initially is positioned as shown in FIG. 5. Skin hook 26 is used to grasp the subcutaneous tissue 36 adjacent the edge 38 of the wound 32. The flat portion 24 of leg 16 is in facing engagement with the outer layer of skin 34 so that the skin 34 and the subcutaneous tissue 36 is grasped between hook 26 and flat serrated surface 24. The instrument is then tilted to evert the skin and expose the subcutaneous tissue for stitching.

A pair of needle holders 40 are used to grasp a needle 42 so as to insert the needle into the subcutaneous tissue 36 to a point where the pointed end 44 protrudes outwardly as shown in FIG. 5. At this point, the instrument 10 is released from its grip on the edge of wound 32, and is used to grasp the free end 44 of needle 42. This is done while needle holders 40 hold the opposite end of needle 42. It is important that needle holders 40 continue to hold needle 42 because without holding the needle 42 in this manner, it is easy to lose the pointed end 44 in the tissue 36, prior to the time that it is grasped.

As seen in FIG. 7, the instrument 10 is able to grasp the free end 44 of needle 42 because hook 26 protrudes within opening 30 so as to permit the serrated flat surfaces 22, 24 to grasp the pointed end 44 of the needle therebetween.

Once instrument 10 has obtained a good grasp on the pointed end 44 of needle 42, it is used to pull the needle completely through to complete the stitch.

From the above, it can be seen that only two instruments are required, i.e., needle holder 40 and instrument 10. In prior instruments utilizing only a skin hook in the place of instrument 10, it was necessary to release the skin hook and to take up a second pair of needle holders for grasping the free end of the needle. Thus, three hands were required, and preferably an assistant was necessary in order to properly do the procedure.

Thus, the device accomplishes at least all of its stated objectives.

What is claimed is:

1. An instrument for skin surgery comprising:
    a Y-shaped member having a central handle portion and first and second diverging leg members, each commencing at said handle portion and diverging downwardly and outwardly therefrom to terminate in a distal end, said distal ends of said first and second leg members being yieldably movable from a normal first position wherein said distal ends are spaced from one another to a second position wherein said distal ends are in engagement with one another;
    said distal ends each including a substantially flat surface, said flat surfaces being presented toward one another so as to engage one another when said leg members are in said first position;
    hook means fixed on said frst leg member adjacent said distal end thereof and spaced inwardly from said distal end, and said hook means extending toward said second leg member and thence upwardly to a point, said point extending generally toward said handle portion.

2. An instrument according to claim 1 wherein said flat surfaces are serrated.

3. A method for using a surgical instrument in making a stitch in an incision in a patient's skin, said instrument comprising a central handle portion and a pair of diverging leg members having distal ends adapted to move from a spread position spaced apart from one another to a closed position in engagement with one another, one of said leg members having a hook therein extending toward the other of said leg members and thence upwardly to terminate in a pointed end extending toward said handle portions, said other leg member having a hole therein sized to receive said hook when said leg members are in said closed position so as to permit said distal ends to engage one another, said skin including an outer skin layer, and a subcutaneous tissue below said skin layer, said method comprising:
    gripping said skin adjacent the edge of said incision between said pair of leg members with said hook retentively engaging said subcutaneous tissue inside said wound and with said distal end of said other leg member engaging the outer surface of said exterior skin layer adjacent said edge of said incision;
    tilting said instrument to evert said skin adjacent said incision with said instrument;
    inserting a surgical needle into said subcutaneous tissue until the pointed end of said needle has passed through a portion of said subcutaneous tissue and has exited therefrom;
    releasing the grip of said skin from between said first and second leg members,
    gripping said pointed end of said needle between said distal ends of said first and second leg members of said instrument whereby said hook is within said hole so as to permit said distal ends to grip said needle;
    using said instrument to pull said pointed end of said needle until said needle exits said subcutaneous tissue.

4. A device according to claim 1 wherein said hook is spaced upwrdly from 3 to 5 millimeters from said distal end of said first leg member.

5. A device according to claim 1 wherein said hole is elongated.

6. A device according to claim 5 wherein said hole is tear drop shaped.

* * * * *